United States Patent [19]
Getz et al.

[11] Patent Number: 5,727,353
[45] Date of Patent: Mar. 17, 1998

[54] PORTABLE MEDICAL DIAGNOSTIC SUITE

[76] Inventors: John E. Getz, 209 Apples Way, Batavia, Ohio 45103; Roy W. Howard, 8284 Woodruff Rd., Cincinnati, Ohio 45255; Maria Janu, 17040 Oak Park Row, Brookfield, Wis. 53005; Charles T. Bergman, Rte. 3, Box 347, Watertown, Wis. 53094

[21] Appl. No.: 627,428

[22] Filed: Apr. 4, 1996

[51] Int. Cl.⁶ ........................................ E04H 3/08
[52] U.S. Cl. ............... 52/79.1; 52/79.5; 52/79.9; 52/143; 296/19; 296/24.1; 62/223; 62/298
[58] Field of Search ................... 52/79.1, 79.5, 52/79.6, 79.9, 79.12, 143; 296/19, 24.1; 62/223, 297, 298

[56] References Cited

U.S. PATENT DOCUMENTS

| | | | |
|---|---|---|---|
| 2,565,997 | 8/1951 | Stone | 296/24.1 X |
| 2,765,499 | 10/1956 | Couse | 52/79.5 X |
| 2,872,792 | 2/1959 | Corhanidis | 62/297 X |
| 3,675,439 | 7/1972 | Maurer | 62/223 |
| 3,792,558 | 2/1974 | Berce et al. | 52/79.12 X |
| 4,181,347 | 1/1980 | Clark | 296/19 X |
| 4,425,978 | 1/1984 | Star | 296/19 X |
| 4,449,746 | 5/1984 | Clark | 296/19 X |
| 4,570,733 | 2/1986 | Star | 180/41 |
| 4,644,705 | 2/1987 | Saccomani et al. | 52/79.5 X |
| 4,712,822 | 12/1987 | Janos et al. | 296/24.1 |
| 4,743,059 | 5/1988 | Legueu | 296/24.1 |
| 4,854,460 | 8/1989 | Josephs | |
| 4,915,435 | 4/1990 | Levine | 296/24.1 |
| 4,998,634 | 3/1991 | Nessfiel | |
| 5,069,143 | 12/1991 | Bunger | 52/79.1 X |
| 5,236,390 | 8/1993 | Young | 296/19 X |
| 5,245,838 | 9/1993 | Cavalea, III | 62/297 X |
| 5,265,748 | 11/1993 | Furukawa | |
| 5,285,604 | 2/1994 | Carlin | 52/79.5 X |

FOREIGN PATENT DOCUMENTS

| | | | |
|---|---|---|---|
| 278626 | 8/1988 | European Pat. Off. | 296/24.1 |
| 1366174 | 6/1964 | France | 296/24.1 |
| 1400050 | 4/1965 | France | 52/79.1 |
| 2125180 | 12/1972 | Germany | 52/79.1 |
| 3-93978 | 4/1991 | Japan | 52/79.5 |

OTHER PUBLICATIONS

Promotional Literature–Ellis & Watts Mobile MR, published in Nov. of 1993.
Promotional Literature–Ellis & Watts Environ IV published in Nov. of 1991.
Magazine Article; Radiology Supplier News, p. 77 on Picker International, Mar. 1996.

*Primary Examiner*—Wynn E. Wood
*Assistant Examiner*—Laura A. Callo
*Attorney, Agent, or Firm*—McCormick, Paulding & Huber

[57] ABSTRACT

A self-contained portable medical diagnostic suite includes an enclosure transportable by a plurality of different modes of shipping and transportation. The enclosure has an exterior surface, and an interior area. Access is provided to the interior area of the enclosure via at least one door. At least one medical diagnostic device is supported within the interior area of the enclosure. A modular climate control system for maintaining the climate in the interior area of the enclosure is removably mounted to the exterior surface of the enclosure. The climate control system can be easily removed from the enclosure's exterior and stored in the interior area during shipment. Integral couplings are provided on the exterior of the enclosure for coupling the enclosure to a load handling device or mode of transportation.

20 Claims, 4 Drawing Sheets

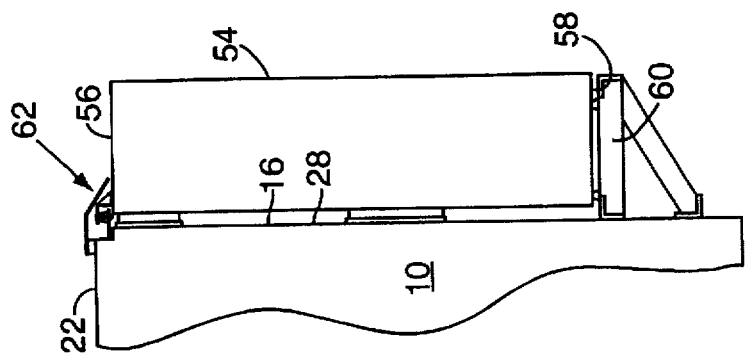
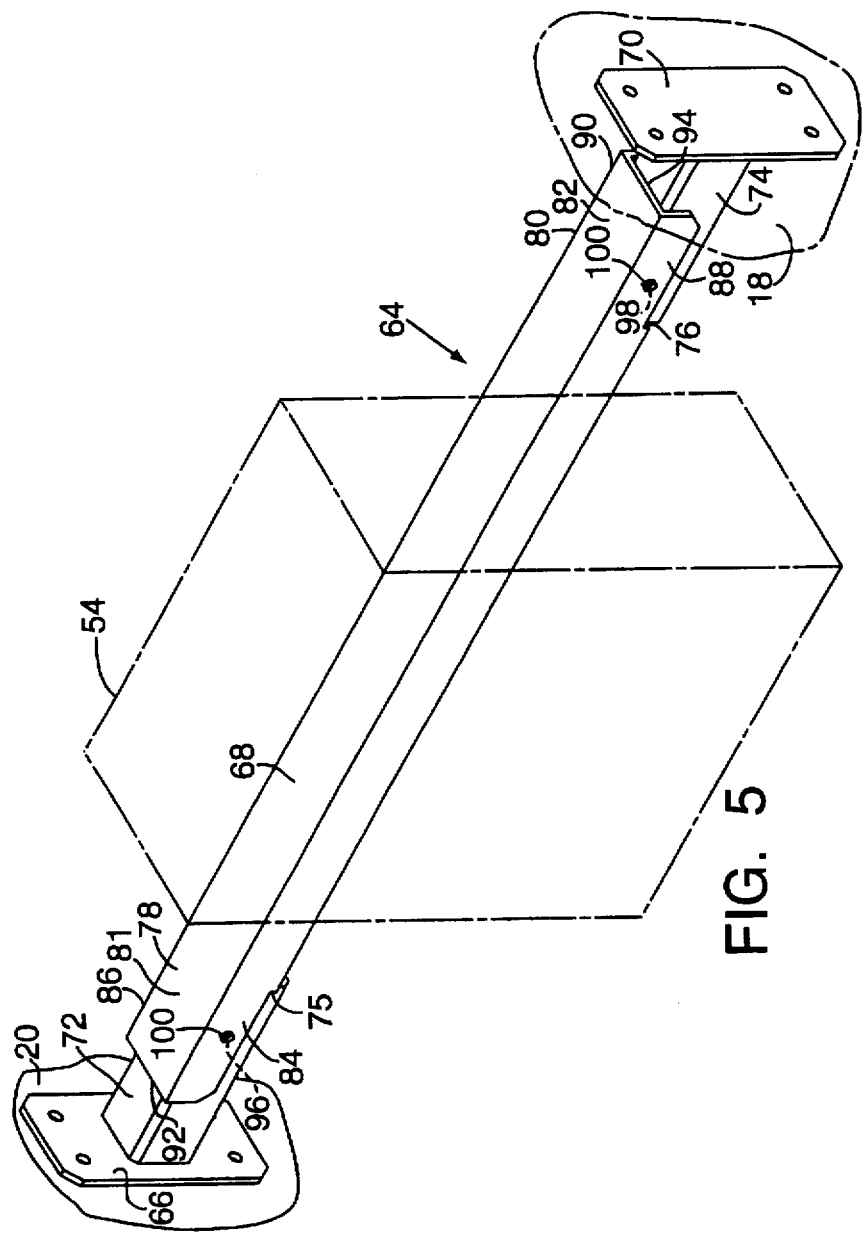

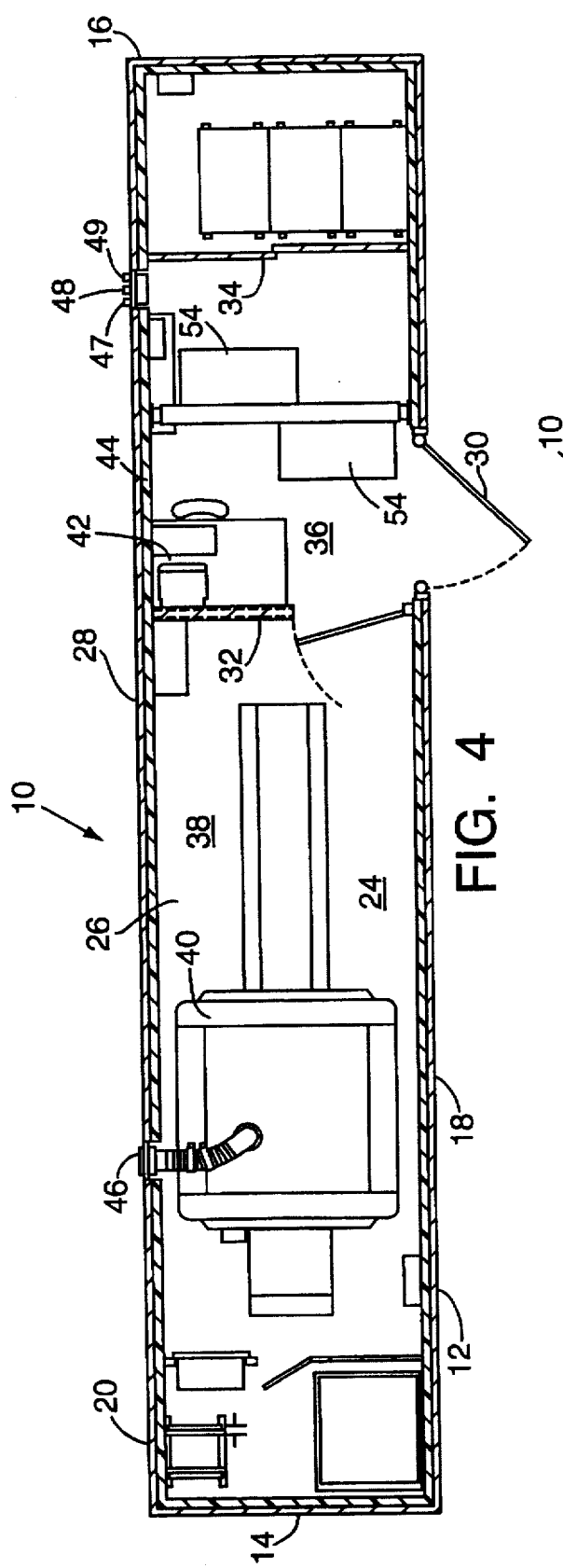

PORTABLE MEDICAL DIAGNOSTIC SUITE

FIELD OF THE INVENTION

The present invention relates to the field of medical diagnostic equipment, and more particularly to a self-contained portable medical diagnostic suite capable of being transported by a plurality of different modes of transportation worldwide.

BACKGROUND OF THE INVENTION

The present invention has particular utility in connection with medical diagnostic equipment installed in a portable self-contained medical suite and is described herein as applied to such use. Advances in technology have provided medical practitioners with an array of diagnostic equipment useful, and often times, invaluable in assessing a patient's condition. However, these diagnostic devices tend to require extensive and expensive site preparation. It can also be prohibitively expensive to transport such equipment. Additionally, a high level of skill is generally needed to install such equipment.

A typical example of the type of equipment referred to is a magnetic resonance imaging system or MRI. Generally MRI's and similar diagnostic equipment like x-ray machinery or CT scanners occupy a great deal of space and can be very heavy. Therefore, existing medical facilities may not have sufficient available floor space to install these devices. In addition, the area where this equipment is located must have floors capable of supporting the large loads imposed by the equipment. Because many of these systems emit various forms of radiation when operated, the facility housing such equipment must be properly shielded to prevent radiation exposure to personnel and other patients. Moreover, these devices are usually operated by sophisticated computerized controls and, therefore, sensitive climate control systems are needed to assure proper function. This peripheral equipment also requires additional space and technical expertise to install.

In the past, it has proven difficult to provide remote areas and underdeveloped countries with this type of diagnostic equipment. In addition to the difficulties associated with getting the equipment to these areas; once the equipment arrives, the skilled labor needed to install the equipment is usually lacking. It may also prove difficult and prohibitively expensive to obtain the necessary construction materials for the installation.

In addition to the foregoing, it is well known in the art to install medical diagnostic suites in conventional trailers or "portable building" type enclosures. However, these systems are not well suited for transport internationally or to remote areas. For example, trailers, used domestically, may not comply with the standards for operation or the requirements for configuration imposed by other countries. Therefore their use could be prohibited in those countries. In addition it may become necessary to transport the trailer by air, rail, or boat in order to reach the more remote areas. However, trailers are not normally equipped to be received by lifting devices such as, for example, cranes. Therefore, loading a trailer onto the aforementioned means of transportation could prove very cumbersome and in some situations may be impossible. The "portable building" type of enclosure would prove even more difficult to transport to international, or remote locations. Generally, these enclosures require trucks adapted to carry wide loads. They cannot be lifted via conventional lifting devices. Moreover, the "portable buildings" are not constructed in such a manner as to enable them to withstand the rigors imposed by international shipment.

In light of the above issues and concerns, there is a current need for a portable, self-contained medical diagnostic suite capable of installation virtually anywhere in the world with little or no skilled labor needed for installation. Such a diagnostic suite must be readily transportable by any number of different modes of transportation and be able to withstand the attendant abuses associated with such transport. In addition, the portable medical diagnostic suite must be capable of reliable function in extreme weather conditions.

Finally, since the diagnostic suite needs to function autonomously, and may be used in any locality in any country, compliance with international design and construction standards is necessary.

Accordingly, the general object of the present invention is to provide a portable self-contained medical diagnostic suite capable of being readily transported anywhere in the world by any conventional mode of transportation.

It is also an object of the present invention to provide a portable self-contained medical diagnostic suite such that once the suite's ultimate destination is reached, it can be made operable with a minimal amount of skilled labor.

It is a further object of the present invention to provide a portable self-contained medical diagnostic suite which complies with international standards and can be easily adapted to the utility service configurations found throughout the world.

SUMMARY OF THE INVENTION

The present invention resides in a portable medical diagnostic suite comprising an enclosure that is capable of being readily transported by a plurality of different shipping and transportation means such as, for example, trains, boats, planes, and trucks. The enclosure has an interior area, an exterior surface, and a means for providing access to the interior area of the enclosure. At least one medical diagnostic device is supported within the interior area of the enclosure, and a modular climate control system for adjustably maintaining the climate of the interior area of the enclosure is removably mounted to the exterior surface of the enclosure. While the medical diagnostic suite is in transit, a means is provided for removably securing the climate control system in the interior area of the enclosure. Integral couplers for connecting the enclosure to a transportation means are provided on the enclosure's exterior surface thereby enabling the transfer and transport of the medical diagnostic suite onto and off of the various modes of transportation.

BRIEF DESCRIPTION OF THE DRAWINGS

FIG. 3 is a side elevation view of a modular climate control system mounted to the exterior of the medical diagnostic suite.

FIG. 4 is a top plan view of the interior of the portable medical diagnostic suite and showing the modular climate control systems mounted in the interior of the suite.

FIG. 4a is a partially sectioned side elevation of the portable medical diagnostic suite.

FIG. 5 is a fragmentary perspective view showing the climate control system securing means.

DETAILED DESCRIPTION OF THE PREFERRED EMBODIMENT

Figure 1:
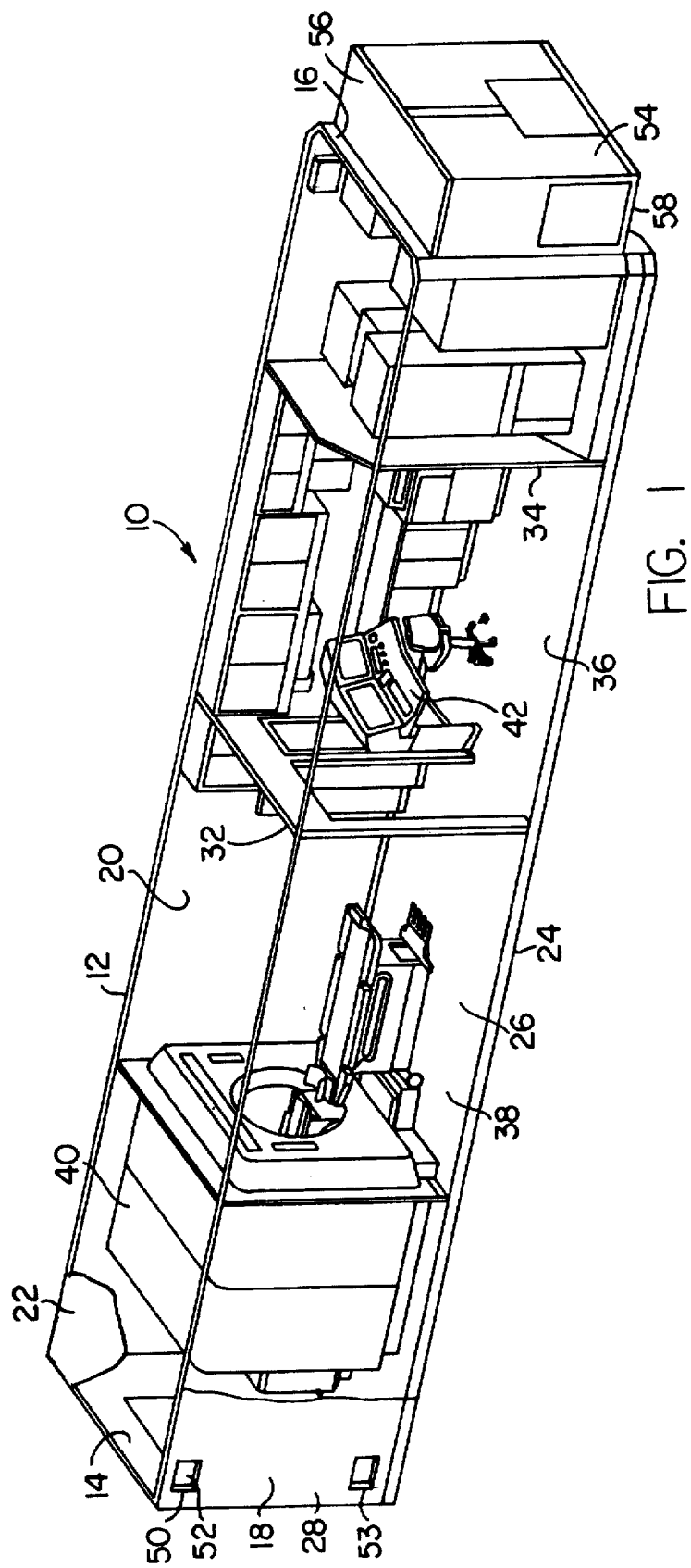
FIG. 1 is a perspective cut away view of a portable medical diagnostic suite.
Figure 2:
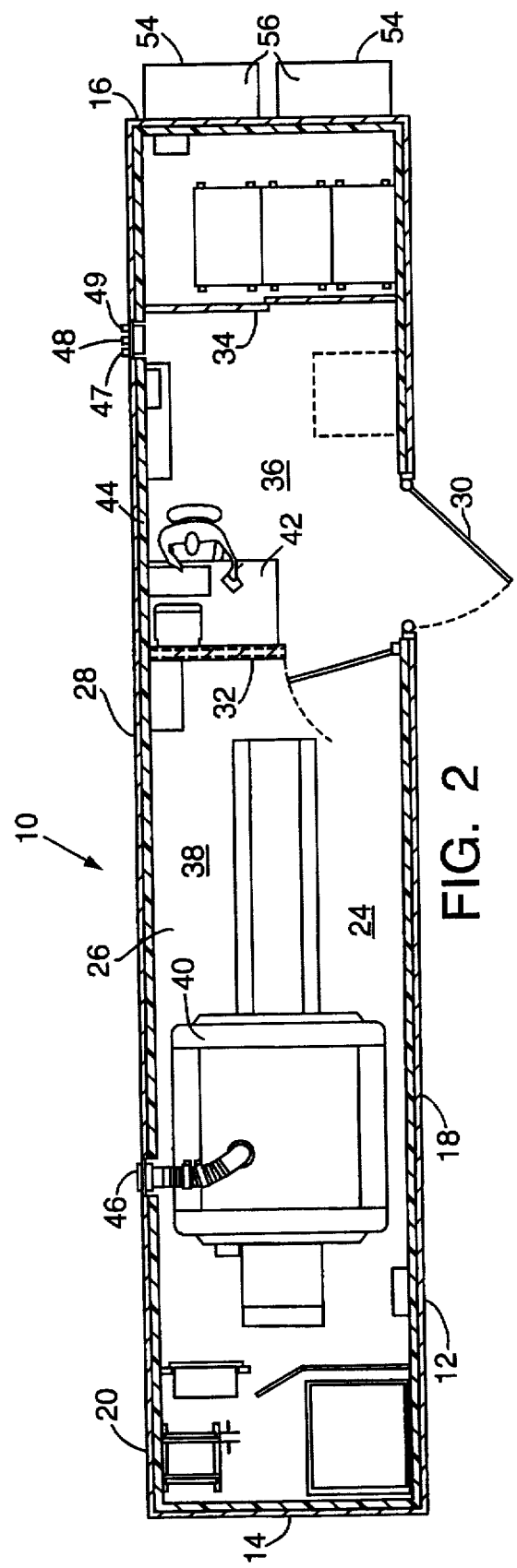
FIG. 2 is a top plan view of the interior of the portable medical diagnostic suite.

Turning to the drawings and first referring to FIG. 1, the preferred embodiment of a portable self-contained medical diagnostic suite, there shown and generally designated as 10, comprises an enclosure 12 having two opposed end walls 14 and 16, two opposed lateral walls 18 and 20, a ceiling 22, and a floor 24 defining an interior area 26 and an exterior surface 28. The described enclosure can take the form of an ISO (International Standards Organization) approved shipping container, but it is to be understood that the present invention is no way limited in this regard. As is best seen in FIG. 2, the enclosure further includes a door 30 for providing access to the interior area of the suite. Interior partitions 32 and 34 are interposed between the lateral walls 18 and 20 and in communication with the ceiling 22 and the floor 24 thereby dividing the interior area 26 into separate sections 36 and 38.

Turning to FIGS. 1, 4 and 4a, a medical diagnostic device 40 shown therein as an MRI is located and supported within separate section 38 and is defined by lateral walls 18 and 20, end wall 14, partition 32, floor 24 and ceiling 22. While an MRI is shown, many other types of medical diagnostic devices known to those skilled in the art may be substituted without departing from the broader aspects of the invention.

An operator's station 42 for controlling the MRI is functionally located in another one of the separate sections 36 of the diagnostic suite 10 and is in operable communication with the MRI.

During Operation, MRI's and other similar medical diagnostic devices emit various forms of radiation. The radiation emitted by the medical diagnostic devices must be contained in order to avoid exposing persons other than the patient to the radiation. In addition, the medical diagnostic devices as well as the controls can influenced from outside sources of radiation, such as, for example radio frequency or RF radiation. Accordingly, walls 18 and 20, end walls 14 and 16, partition 32, floor 24 and ceiling 22 are covered with radiation insulation 44 which prevents both the egress and ingress of radiation. Thus, an operator can control the various functions of the MRI from a remote location completely shielded from both the radiation emitted by the device and any radiation emitted from sources external to the diagnostic suite.

An MRI requires a plurality of different utility services in order to properly function. As shown in FIG. 4, a gas connection 46, a telephone connection 47 an electrical connection 48 and a data connection 49 are shown extending through the lateral wall 20. It is to be understood that different service connectors are required for different types of equipment. Moreover, service utilities of varying configurations are found in different installation locales. Thus, the suite 10 is provided with service connectors readily adaptable to all such utility service configurations.

Referring back to FIG. 1 the enclosure 12 has integral lifting holes 50 extending through the exterior surface 28 for coupling the enclosure 12 to a load handling device (not shown), thereby enabling the transfer of the medical diagnostic suite 10 onto and off of the aforementioned plurality of transportation means. The lifting holes 50 have inner peripheries 52. The inner peripheries 52 are reinforced such that when the load handling device is coupled to the lifting holes 50, the inner peripheries 52 of the lifting holes 50 are capable of carrying the entire weight of the medical diagnostic suite 10. It should be understood that while lifting holes are shown and described, many other types of couplers known to those skilled in the art, such as, for example, rectangular channels sized and positioned to fit the tines of a fork lift, industrial shackles, and industrial eyebolts, may be substituted without departing from the broader aspects of the invention. In addition to the aforementioned lifting holes, the enclosure 12 has integral retaining holes 53 extending through the exterior surface 28 for coupling the medical diagnostic suite 10 to a plurality of different transportation means such as, for example, a trailer, railroad car, boat, or plane. As with the lifting holes, it should be understood that while retaining holes are shown and described, many other types of couplers known to those skilled in the art may be substituted without departing from the broader aspects of the invention.

Referring now to FIGS. 1, 2 and 3, a modular climate control system 54 having a top surface 56, and a bottom surface 58, for adjustably maintaining the climate of the interior area 26 is removably mounted to the exterior surface 28 by a mounting device. The mounting device comprises a brace member 62 and mounting bracket 60 fastened to the enclosure end wall 16. As can best be seen in FIG. 3, the bottom surface 58 of the climate control system 54 is removably attached to the bracket 60. The brace member 62 is interposed between and removably fastened to the top surface 56 of the climate control system 54 and the end wall 16 thereby securing the modular climate control system to the enclosure 12.

As shown in FIG. 4, when in transit, the modular climate control system 54 is stored inside of the enclosure. A securing device 64 for removably securing the climate control system 54 within the interior area 26 is interposed between and connected to the lateral walls 18 and 20. During transit of the medical diagnostic suite, the climate control system 54 is removably attached to the securing device 64 such that the system is prevented from shifting within the enclosure's interior area 26, thereby preserving the operational integrity of the climate control system 54.

The climate control system securing device 64 referred to above and shown in FIG. 5 comprises a pair of opposed brackets 66 and 70 removably mounted to lateral walls 18 and 20, and having outwardly extending members 72, and 74. A mounting bar 68 having opposed ends 75 and 76 is interposed between the brackets 66 and 70. A channel section 78 and 80 extends from each of the opposed ends 75 and 76. The channel sections 78 and 80 have top surfaces 81 and 82 and opposed side walls 84, 86, 88, and 90 which depend downwardly from the top surfaces 80 and 82 respectively. The sidewalls 84, 86, 88, and 90 and the top surfaces 80 and 82 cooperate to define interior channel areas 92 and 94. Interior channel areas 92 and 94 are shaped to receive the outwardlly extending members 72 and 74 of the oppossed brackets 66 and 70 such that the mounting bar 68, when installed, snugly fits over the outwardly extending members 72 and 74. Bores 96 and 98 extend through the channel sections 80 and 82 and through the outwardly extending members 72 and 74 on the opposed brackets 66 and 70. Fasteners 100 extend through the bores 96 and 98 thereby removably securing the mounting bar 68 to the opposed brackets 66 and 70. The fasteners 100 can be any type of fastener known to those skilled in the art, such as, for example a bolt and nut, or a pin. As explained previously, when the medical diagnostic suite 10 is in transit, the modular climate control system is removably attached to the mounting bar 68. However, once the portable medical diagnostic suite has reached its final destination, the modular climate control system 54 is removed from the mounting bar 68 and is removably mounted to the exterior surface 28 of the enclosure 12. Mounting bar 68, and brackets 66 and 70 can then be removed and stored such that the interior area 26 of the diagnostic suite 10 is not obstructed.

It is to be understood that the form of the invention shown and described herein is to be taken as a preferred embodiment of the same, and that various changes in the selection of parts comprising the broadly defined means and in the arrangement of said parts may be resorted to without departing from the spirit of the invention or the scope of the following claims.

We claim:

1. A self-contained portable medical diagnostic suite comprising:

an enclosure in the form of a shipping container transportable by a plurality of different shipping and transportation means, said enclosure defining an exterior surface, an interior area, and including at least one door for providing access to the interior area of the enclosure;

at least one medical diagnostic device supported within the interior area of the enclosure;

a modular climate control system for adjustably maintaining the climate of the interior area;

a mounting device for removably mounting said modular climate control system to the exterior surface of said enclosure;

a securing device for removably securing said climate control system within said interior area during transit of said suite;

a controller in communication with and for operating said at least one medical diagnostic device; and a coupler integral with said enclosure for coupling the enclosure to a load handling device thereby enabling the transfer of said suite onto and off of said plurality of transportation means.

2. The self-contained portable medical diagnostic suite of claim 1 further comprising an operator's station for operating said at least one medical diagnostic device, said operator's station being functionally located in said interior area of said enclosure and in operable communication with said at least one medical diagnostic device.

3. The self-contained portable medical diagnostic suite of claim 1 further comprising:

at least one interior partition for dividing said interior area of said enclosure into at least one separate interior section;

said at least one medical diagnostic device being located in at least one of said separate sections; and at least one operator's station functionally located in another of said separate sections and in operable communication with said at least one medical diagnostic device.

4. The self-contained portable medical diagnostic suite of claim 1 wherein said mounting device comprises:

a mounting frame removably mounted to said enclosure exterior surface for supporting said climate control system; and a brace fastened to said climate control system and said enclosure thereby securing said climate control system to said enclosure.

5. The self-contained portable medical diagnostic suite of claim 1 wherein said securing device comprises:

a pair of opposed brackets removably mounted to said interior surface of the enclosure;

an elongated mounting bar interposed between and removably attached to said opposed brackets; and said bar being removably fastened to said climate control system to secure said system in a fixed position during transit of said suite.

6. The self-contained portable medical diagnostic suite of claim 5 wherein, said elongated mounting bar has opposed ends and channel shaped sections extending from each of said opposed ends, said channel shaped sections having a top surface and opposed side surfaces;

said brackets having an outwardly extending mounting member receivable between said opposed side surfaces of said mounting bar channel shaped sections;

each of said channel shaped sections and said outwardly extending members having a bore extending therethrough; and a fastener extending through said bores thereby removably securing said mounting bar to said brackets.

7. The self-contained portable medical diagnostic suite of claim 5 wherein:

said interior section where said at least one medical diagnostic device is located is shielded to prevent the emission of radiation outside of said section.

8. The self-contained portable medical diagnostic suite of claim 1 further comprising connectors for operably connecting said at least one medical diagnostic device to a plurality of different utility services.

9. The self-contained portable medical diagnostic suite of claim 1 wherein said exterior surface of said enclosure defines at least one lifting hole having a reinforced inner periphery capable of supporting the entire weight of said suite for coupling said suite to said load handling device.

10. The self contained portable medical diagnostic suite of claim 1 wherein said integral coupler comprises at least one pair of rectangular channels fixed to said exterior surface of the enclosure, said channels being sized and positioned to receive the tines of a fork lift.

11. The self-contained portable medical diagnostic suite of claim 1 wherein said integral coupler comprises at least one pair of industrial shackles fixed to said exterior of said enclosure.

12. The self-contained portable medical diagnostic suite of claim 1 wherein said integral coupler comprises at least one pair of conventional industrial eyebolts fixed to said exterior of said enclosure.

13. The self-contained portable medical diagnostic suite of claim 1 wherein said at least one medical diagnostic device emits one of a number of different forms of radiation, and wherein said interior of said enclosure is shielded to prevent the emission of said radiation outside of said enclosure interior as well as to prevent the ingress of radiation from sources outside of said enclosure.

14. A self-contained portable medical diagnostic suite comprising:

a shipping container transportable by a plurality of different transportation means, said shipping container being defined by two opposed end walls, two opposed lateral walls, a ceiling, and a floor defining an interior area and an exterior surface;

said shipping container including at least one door for providing access to said interior area;

at least one medical diagnostic device supported within said interior area of said shipping container;

at least one interior partition interposed between said lateral walls and in communication with said ceiling and said floor for dividing said interior area of said shipping container into at least one separate section;

said at least one medical diagnostic device being located in at least one of said separate sections;

at least one operator's station for operating said one or more medical diagnostic devices functionally located in another one of said separate sections of said shipping container and in operable communication with said one or more medical diagnostic devices;

at least one connector for connecting said at least one medical diagnostic device to a plurality of different utility services;

said exterior of said shipping container having at least one integral lifting hole, for coupling said shipping container to a load handling device, thereby enabling the transfer of said suite onto and off of said plurality of shipping and transportation means;

a modular climate control system for adjustably maintaining the climate of said interior area;

a mounting device for removably mounting said modular climate control system to the exterior surface of said enclosure; and a securing device for removably securing said climate control system within said interior area during transit of said suite.

15. The self-contained portable medical diagnostic suite of claim 14 wherein said securing device comprises:

a pair of opposed brackets, each bracket having an outwardly extending mounting member, said brackets being removably mounted to said interior surface of the enclosure;

an elongated mounting bar interposed between said brackets and having opposed ends and channel shaped sections extending from each of said opposed ends, said channel shaped sections having a top surface and opposed side surfaces;

said outwardly extending members on said brackets being receivable between said opposed side surfaces of said mounting bar channel shaped sections;

each of said channel shaped sections and said outwardly extending members having a bore extending therethrough;

a fastener extending through each of said bores thereby removably securing said mounting bar to said brackets; and said mounting bar being removably fastened to said climate control system to secure said system in a fixed position during transit of said suite.

16. The self-contained portable medical diagnostic suite of claim 14 wherein said mounting device comprises:

a mounting frame removably mounted to said enclosure exterior surface for supporting said climate control system; and a brace fastened to said climate control system and said enclosure thereby securing said climate control system to said enclosure.

17. The self-contained portable medical diagnostic suite of claim 14 wherein said at least one medical diagnostic device emits one of a number of different forms of radiation.

18. The self-contained portable medical diagnostic suite of claim 14 wherein said separate areas where said at least one medical diagnostic device is located is shielded to prevent the emission of said radiation.

19. The self-contained portable medical diagnostic suite of claim 14 wherein said at least one medical diagnostic device comprises a magnetic resonance imaging system (MRI).

20. The self-contained portable medical diagnostic suite of claim 14 wherein said two opposed end walls, said two opposed lateral walls, said ceiling, and said floor are shielded to prevent the ingress of radiation from sources external to said suite.

* * * * *